United States Patent [19]
Banchereau et al.

[11] Patent Number: 5,608,103
[45] Date of Patent: Mar. 4, 1997

[54] PREPARATION OF ALKANESULPHONIC ACIDS BY PHOTOOXIDATION OF SULPHER-CONTAINING DERIVATIVES

[75] Inventors: Evelyne Banchereau, Billere; Sylvie Lacombe, Artiguelouve; Jean Ollivier, Arudy, all of France

[73] Assignee: Elf Atochem S.A., France

[21] Appl. No.: 565,613

[22] Filed: Nov. 29, 1995

[30] Foreign Application Priority Data

Nov. 29, 1994 [FR] France ................................. 94 14279

[51] Int. Cl.$^6$ ................................. C07C 309/04
[52] U.S. Cl. ................................. 562/115
[58] Field of Search ................................. 562/115

[56] References Cited

U.S. PATENT DOCUMENTS 2,697,722 12/1954 Johnson et al. .
3,392,095 7/1963 Dimond et al. .

OTHER PUBLICATIONS

Journal Of Organic Chemistry, vol. 37, No. 22, 3 Nov. 1972, pp. 3516–3520, R. W. Murray et al.

Tetrahedron Letters, vol. 35, No. 27, 4 Jul. 1994, pp. 4723–4726, E. L. Clennan et al.

*Primary Examiner*—Joseph Conrad

[57] ABSTRACT

The invention relates to the preparation of alkanesulphonic acids by photooxidation of sulphur-containing derivatives (thiols, sulphides, disulphides).

The operation is carried out in solution in aqueous or alcoholic acetonitrile, with a light source irradiating between 200 and 400 nm.

9 Claims, No Drawings

PREPARATION OF ALKANESULPHONIC ACIDS BY PHOTOOXIDATION OF SULPHER-CONTAINING DERIVATIVES

FIELD OF THE INVENTION

The present invention relates to the synthesis of alkanesulphonic acids and its subject is, more particularly, the preparation of $C_1$ to $C_4$ alkanesulphonic acids from the corresponding sulphur-containing derivatives.

BACKGROUND OF THE INVENTION

The alkanesulphonic acids and their salts have numerous industrial applications, especially as detergents, emulsifiers, esterification catalysts and hardeners for some resins.

Industrially, alkanesulphonic acids are most often produced from alkanes by sulphonation or by chlorosulphonation. These two routes of synthesis have, however, the disadvantage of leading to the formation of by-products which are sulphonated on the various carbon atoms of the hydrocarbon chain. Moreover, the hydrolysis of alkanesulphonyl chlorides generally leads to alkanesulphonic acids which are more or less intensely coloured and to the undesired production of hydrochloric acid.

In the last few years, much work has been devoted to the atmospheric photochemistry of sulphur-containing organic compounds (thiols, sulphites, disulphites) which are, in trace amounts, atmospheric constituents of biogenic origin, or, more often, pollutants arising from energy production technologies. Most of these photochemical studies were carried out in the gas phase at low pressure ($\leq 1$ atm) in the presence of air, oxygen, an eluent gas and sometimes nitrogen oxides. All the results obtained mention the formation of sulphur dioxide and sulphonic and sulphuric acids, as well as other products which vary according to the conditions employed.

Research into solution photooxidation of sulphur-containing organic compounds has almost exclusively been devoted to the photooxidation of sulphides in the presence of photosensitizers for the preparation of sulphoxides and sulphones. Two articles, one by R. W. Murray et al. (J. Org. Chem. Soc., 37, 1972, pp. 3516–3520) and the other by E. L. Clennan et al. (Tetrahedron Lett., 35, 1994, pp. 4723–6) relate to the formation of thiosulphinates and of thiosulphonates by photooxidation of disulphides in the presence of photosensitizers.

DESCRIPTION OF THE INVENTION

It has now been found that excellent yields of alkanesulphonic acids may be obtained from thiols, sulphides and disulphides by photooxidation in the presence of oxygen without a catalyst if the procedure is carried out in solution in aqueous or alcoholic acetonitrile with a light source irradiating between 200 and 400 nm.

The subject of the invention is thus a process for the preparation of an alkanesulphonic acid R—$SO_3H$ from a corresponding sulphur-containing derivative R—S—X, X representing a hydrogen atom, an alkyl radical R or an alkylthio group —SR, characterized in that it consists in submitting a solution of the sulphur-containing derivative in aqueous or alcoholic acetonitrile, in the presence of oxygen, to an irradiation by light rays of wavelength between 200 and 400 nm.

The process according to the invention applies more particularly to the synthesis of alkanesulphonic acids for which the hydrocarbon chain, which may be linear or branched, may contain from 1 to 4 carbon atoms. Dimethyl sulphide, dimethyl disulphide, diethyl disulphide, dipropyl disulphide, n-butanethiol, di-n-butyl sulphide, di-n-butyl disulphide and di-tert-butyl disulphide may be mentioned, without implied limitation, as examples of sulphur-containing derivatives to be used as starting materials.

The concentration of sulphur-containing derivative in the starting reaction solution may generally range from 0.01 to 5 mol/liter but it is preferably between 0.05 and 0.5 mol/liter.

The amount of water or of alcohol in the reaction solution may vary within wide limits. It may range up to 100 mol per mole of sulphur-containing derivative but is preferably between 1 and 50 mol per mole of sulphur-containing derivative. A $C_1$ to $C_4$ alcohol, and more particularly methanol, is preferably used as alcohol.

Oxygen, which is necessary for the reaction, may be provided in pure form or diluted by an inert gas such as, for example, nitrogen. The oxygen is preferably introduced gradually into the reaction solution. The total amount of oxygen needed is at least 2 mol per mole of thiol or of sulphide present in the initial solution and at least 4 mol per mole of disulphide. It is preferred to carry out the procedure with an oxygen excess of at least 50%.

The photooxidation according to the invention may be conducted at a temperature between $-20°$ C. and the boiling point of the reaction mixture, but the procedure is preferably carried out between $5°$ and $45°$ C. The operation is advantageously performed at atmospheric pressure, but it would not be departing from the scope of the present invention to work under pressure.

The process according to the invention may be implemented in a batchwise or continuous manner, in any photochemical reactor, for example in an immersion or a falling-film reactor fitted with one or more low, medium or high pressure mercury vapour lamps or excimer lamps emitting in the ultraviolet region.

EXAMPLES

The examples which follow illustrate the invention without, however, any limitation being implied.

Example 1

A photochemical reactor fitted with a central immersion lamp holder is used. The light source is a 450 W medium pressure mercury Hanovia lamp (reference 679 A) and the lamp holder used is made of quartz. With this lamp holder, the volume of liquid in the reactor is 250 ml and the light path is 6.5 mm. The reactor and the lamp holder are thermostated by ordinary water circulation and oxygen is introduced at atmospheric pressure via the base of the reactor through a sinter (porosity 4). To minimize entrainment of volatile products, the gaseous effluent at the reactor outlet passes through a water-cooled condenser; it is then admitted into a bubbler containing sodium hydroxide and finally directed towards a flare.

250 ml of a 0.2M dimethyl disulphide solution (i.e. 0.05 mol of DMDS) in acetonitrile containing 27 ml of water were introduced into the reactor. The solution was left over an oxygen sparge (flow rate: 2.8 liters/hour) for 5 to 10 minutes at $15°$ C., the lamp was then lit and, while maintaining the same oxygen flow rate, irradiation was carried out for 2 hours and 45 minutes at $35°$–$40°$ C.

After this period, the solution was clear and homogeneous and no precipitate was found to be present. After evaporation of the solvent, 17.3 g of a colorless liquid were obtained for which the potentiometric, gravimetric and $^1$H NMR analyses indicated almost complete conversion (98%) of the DMDS with a methanesulphonic acid (MSA) yield of 62% and a sulphuric acid yield of 19%.

Example 2 (Comparative)

Example 1 was repeated, but using 250 ml of a 0.2M DMDS solution in anhydrous acetonitrile and continuing to irradiate for 4 hours and 15 minutes.

After evaporation of the solvent, 7.7 g of a brown, non-homogeneous crude product were obtained for which the analysis, after taking up in water and extraction with chloroform, indicated complete conversion (100%) of the DMDS with a methanesulphonic acid yield of 44% and a sulphuric acid yield of 1.2%.

Examples 3 to 10

Example 1 was repeated, but varying the amount of water. The results obtained are collected in the following Table I.

TABLE I

| | EXAMPLE | | | | | | | |
|---|---|---|---|---|---|---|---|---|
| | 3 | 4 | 5 | 6 | 7 | 8 | 9 | 10 |
| Amount of water (ml) | 0.9 | 1.8 | 1.8 | 2.7 | 9.9 | 18 | 57.6 | 90 |
| Irradiation time (hours and minutes) | 3 h | 1 h 30 | 3 h 30 | 3 h 30 | 3 h | 2 h 45 | 2 h 40 | 3 h |
| Degree of conversion of DMDS (%) | 98 | 60 | 99 | 99 | 99 | 98 | 100 | 100 |
| MSA yield (%) | 44 | 55* | 57 | 55 | 66 | 70 | 62 | 44.1 |
| Sulphuric acid yield (%) | 4 | 3.4* | 10 | 14 | 19 | 18 | 21 | 21.5 |

*Yield with respect to DMDS consumed

Examples 11 to 14

The procedure was carried out as in Example 1, but replacing DMDS with the same molar amount of other dialkyl disulphides R—SS—R and using only 1.8 ml of water (2 mol per mole of disulphide). The results obtained are collected in the following table.

TABLE II

| | EXAMPLE | | | |
|---|---|---|---|---|
| | 11 | 12 | 13 | 14 |
| Alkyl radical R | $C_2H_5$ | $n\text{-}C_3H_7$ | $n\text{-}C_4H_9$ | $t\text{-}C_4H_9$ |
| Irradiation time (hours and minutes) | 4 h 30 | 4 h | 4 h 30 | 6 h |
| Degree of conversion of the disulphide (%) | 100* | 100** | 100* | 100 |
| Yield of the acid R—$SO_3H$ (%) | 49 | 46 | 56 | 50 |
| Sulphuric acid yield (%) | 17.1 | 16 | 13 | 16 |

*after 3 h 30
**after 3 h

Examples 15 and 16

The procedure was carried out as in Example 1, but replacing DMDS with the same molar amount of di-n-butyl sulphide (Example 15) or n-butanethiol (Example 16) and using only 1.8 ml of water (2 mol per mole of sulphur-containing derivative).

The results obtained are collected in the following Table III.

TABLE III

| | EXAMPLE | |
|---|---|---|
| | 15 | 16 |
| Irradiation time (hours) | 3 h | 3 h |
| Degree of conversion of the sulphur-containing derivative (%) | 100 (at 2 h) | 100 (at 2 h) |
| n-Butanesulphonic acid yield (%) | 50 | 63 |
| Sulphuric acid yield (%) | 10.4 | 21 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the preparation of an alkanesulphonic acid R—$SO_3H$ from a corresponding sulphur-containing derivative R—S—X, X representing a hydrogen atom, an alkyl radical R or an alkylthio group —SR, comprising submitting a solution of the sulphur-containing derivative in aqueous or alcoholic acetonitrile, in the presence of oxygen, to an irradiation by light rays of wavelength between 200 and 400 nm, in which the alkyl radical or radicals R of the sulphur-containing derivatives are linear or branched alkyl radicals containing from 1 to 4 carbon atoms.

2. Process according to claim 1, wherein the concentration of sulphur-containing derivative in the starting reaction solution may range from 0.01 to 5 mol/liter.

3. Process according to claim 2, wherein the range is between 0.05 and 0.5 mol/liter.

4. Process according to one claim 1, wherein the amount of water or alcohol in the reaction solution is between 1 and 100 mol per mole of sulphur-containing derivative.

5. Process according to claim 4, wherein the amount is between 1 and 50 mol.

6. Process according to claim 1, wherein the procedure is carried out at a temperature between −20° C. and the boiling point of the reaction mixture.

7. Process according to claim 6, wherein the temperature is between 5° and 45° C.

8. Process according to claim 1, wherein the procedure is carried out at atmospheric pressure or under pressure.

9. Process according to claim 1, wherein methanesulphonic acid is synthesized from dimethyl disulphide.

* * * * *